United States Patent [19]
Heath et al.

[11] Patent Number: 5,713,736
[45] Date of Patent: Feb. 3, 1998

[54] ENDODONTIC DENTAL INSTRUMENT

[75] Inventors: Derek E. Heath; Jerry A. Mooneyhan, both of Johnson City, Tenn.

[73] Assignee: Tulsa Dental Products, L.L.C., Tulsa, Okla.

[21] Appl. No.: 641,497

[22] Filed: May 1, 1996

[51] Int. Cl.$^6$ ........................................... A61C 5/02
[52] U.S. Cl. ........................................... 433/102; 408/230
[58] Field of Search ........................... 4330/102, 165, 4330/224; 408/227, 230; 606/80

[56] References Cited

U.S. PATENT DOCUMENTS

| | | | |
|---|---|---|---|
| 2,370,706 | 3/1945 | Andreasson | 408/230 |
| 3,045,513 | 7/1962 | Andreasson | 408/230 |
| 4,871,312 | 10/1989 | Heath | 433/102 |
| 4,934,934 | 6/1990 | Arpaio, Jr. et al. | |
| 5,106,298 | 4/1992 | Heath et al. | |
| 5,464,362 | 11/1995 | Heath et al. | |

FOREIGN PATENT DOCUMENTS

| | | | |
|---|---|---|---|
| 3545586 | 7/1987 | Germany | 408/230 |
| 637207 | 12/1978 | U.S.S.R. | 408/230 |

*Primary Examiner*—Gene Mancene
*Assistant Examiner*—Ralph Lewis
*Attorney, Agent, or Firm*—Bell Seltzer Intellectual Property Law Group of Alston & Bird LLP

[57] ABSTRACT

An endodontic instrument which comprises an elongate shank which has a tapered working length adjacent the pilot end, and at least two continuous helical flutes formed along the tapered working length. The flutes are non-uniformly separated in the axial direction, and they define a relatively broad helical land and at least one relatively narrow helical surface. In one embodiment, the helical surface is a relatively narrow helical land and in another embodiment, the helical surface is a sharp helical edge.

20 Claims, 2 Drawing Sheets

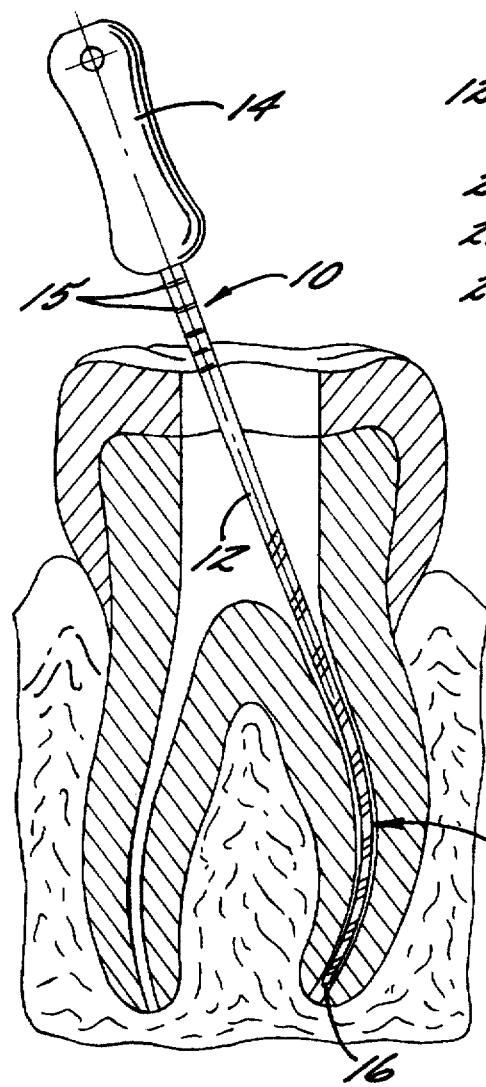
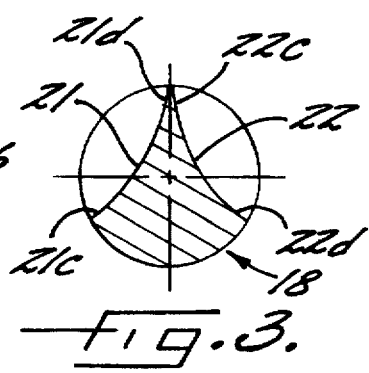
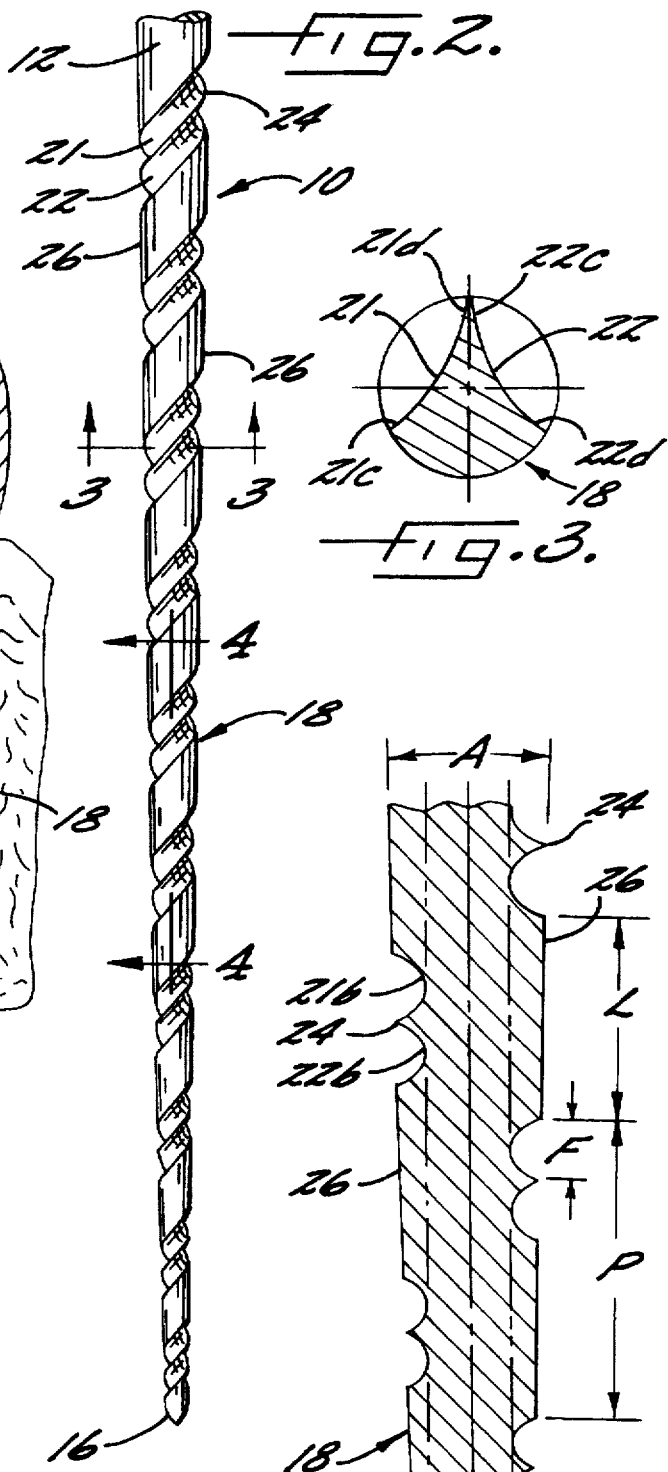
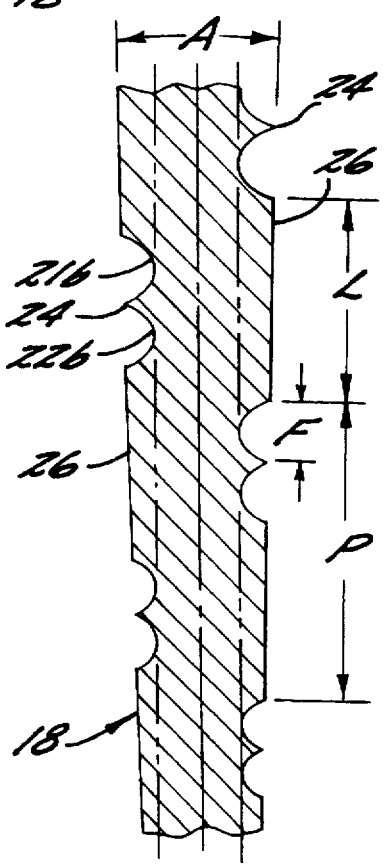

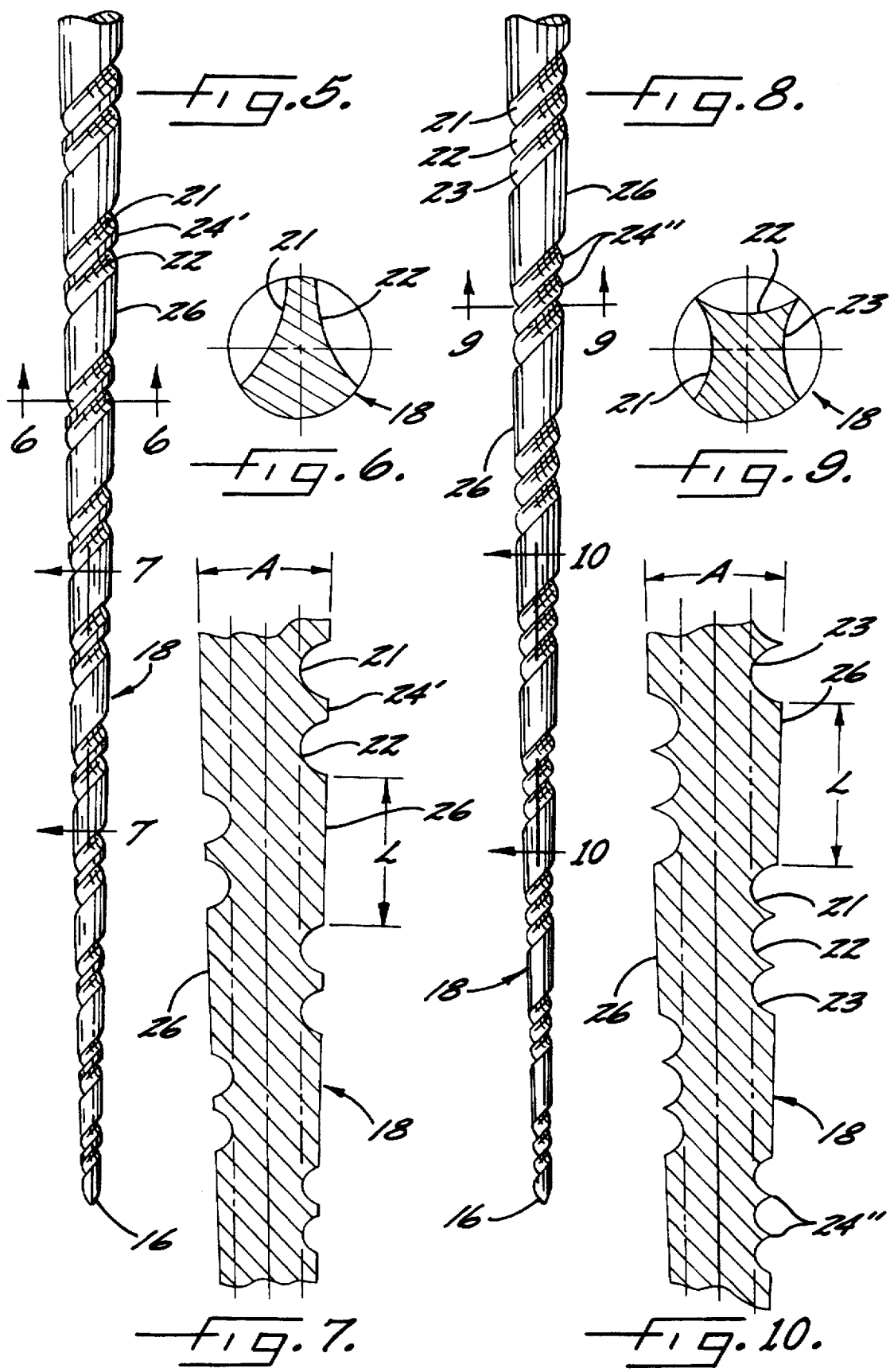

5,713,736

1

ENDODONTIC DENTAL INSTRUMENT

BACKGROUND OF THE INVENTION

The present invention relates to an endodontic instrument adapted for use in performing root canal therapy on teeth.

Root canal therapy is a well-known procedure wherein the crown of the diseased tooth is opened so as to permit the canal to be cleaned and then filled. More particularly, a series of very delicate, flexible, instruments or files are used to clean out and shape the root canal, and each file is rotated and reciprocated in the canal by the dentist, either manually or with the use of a dental handpiece which mounts the file. Files of increasingly larger diameter are used in sequence, to achieve the desired cleaning and shaping. When the canal is thus prepared, it is solidly filled with a filling material, which typically comprises a waxy, rubbery compound known as gutta percha. In one procedure, the gutta percha is positioned on an instrument called a compactor, and the coated compactor is inserted into the prepared canal and rotated and reciprocated to compact the gutta percha therein. The dentist thereafter fills the tooth above the gutta percha with a protective cement, and lastly, a crown may be fitted to the tooth.

Endodontic files of the described type are fully disclosed in U.S. Pat. Nos. 4,934,934; 5,106,298; and 5,464,362, the disclosures of which are incorporated herein by reference. Such files comprise an elongate rod-like shank having a handle at one end, and with one or more, up to four, helical flutes formed in the peripheral surface of the shank. The files are commonly supplied to the clinician in kits which comprise several files of increasing diameter. In particular, and in accordance with ANSI/ADA Specification No. 28-1988, files are provided in diameters which range from 0.08 mm at the tip (size 08) to 1.40 mm at the tip (size 140), and the files are provided in kits which contain a number of files of increasing diameter so that the files from a particular kit may be used in sequence by the clinician in accordance with the requirements of the particular canal being cleaned.

The helical flutes in the peripheral surface of the shank are commonly separated in the axial direction so as to define helical lands between axially adjacent flute segments. As noted, for example, in the above-referenced U.S. Pat. No. 5,106,298, the lands are helpful in preventing undue cutting by the instrument laterally into the wall of the canal during rotation, and guiding the instrument centrally along the canal.

It is an object of the present invention to provide an improved endodontic instrument of the described type and which permits the functional operation of the instrument to be selected to fit particular requirements. For example, it may be desirable in particular applications to provide the instrument with more strength and less flexibility than is provided by conventional instruments. It may also be desirable in particular applications to further minimize the tendency for lateral cutting of the canal.

SUMMARY OF THE INVENTION

The above and other objects and advantages of the present invention are achieved in the embodiments illustrated herein by the provision of an endodontic instrument which comprises an elongate shank having a proximate end and an opposite pilot end, and a working length adjacent the pilot end which includes a peripheral surface. The instrument also has a plurality of continuous helical flutes formed in the peripheral surface so as to extend along the length of the working length, with all of the flutes having the same helix angle, and comprising a first flute, and a second flute closely adjacent the first flute on the side of the first flute toward the pilot end so as to define a relatively narrow helical surface therebetween, and a relatively broad helical land disposed between the second flute and the first flute in a direction from the second flute toward the pilot end.

In one embodiment, the relatively narrow helical surface comprises a relatively sharp helical edge, and in another embodiment, the relatively narrow helical surface comprises a second helical land which has an axial dimension which is significantly less than the axial dimension of the first mentioned helical land.

BRIEF DESCRIPTION OF THE DRAWINGS

Some of the objects and advantages of the present invention having been stated, others will appear as the description proceeds, when taken in conjunction with the accompanying drawings, in which FIG. 1 is a sectional view of a tooth having two roots, with an endodontic instrument which embodies the present invention received in one of the roots.

FIG. 2 is an enlarged perspective view of the working length of the instrument shown in FIG. 1;

FIG. 3 is a transverse sectional view taken substantially along the line 3—3 of FIG. 2;

FIG. 4 is a longitudinal sectional view taken substantially along the line 4—4 of FIG. 2;

FIG. 5 is a perspective view of the working length of a second embodiment of an endodontic instrument in accordance with the present invention;

FIG. 6 is a transverse sectional view taken substantially along the line 6—6 of FIG. 5;

FIG. 7 is a longitudinal sectional view taken substantially along the line 7—7 of FIG. 5;

FIG. 8 is a perspective view of the working length of a third embodiment of the invention;

FIG. 9 is a transverse sectional view taken substantially along the line 9—9 of FIG. 8; and FIG. 10 is a transverse sectional view taken substantially along the line 10—10 of FIG. 8.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, this embodiment is provided so that this disclosure will be thorough and complete and will fully convey the scope of the invention to those skilled in the art. Like numbers refer to like elements throughout.

Referring more particularly to FIGS. 1–4, an endodontic instrument 10 is illustrated which comprises a shank 12 which is preferably composed of a metallic material such as stainless steel, or nickel-titanium alloy as described in U.S. Pat. No. 5,464,362. In one preferred embodiment, the shank is composed of an alloy comprising at least about 40% titanium and at least about 50% nickel. Also, the shank 12 is of circular cross-sectional configuration, and it typically has a length of about 30 mm (1.2 inches). The shank also includes an outer or proximate end which mounts a conventional handle 14, which is configured for hand engagement, and the portion of the shank immediately below the handle includes calibrated depth markings 15 of conventional design. The shank further includes an opposite distal or pilot end 16, and a tapered working length 18 is defined adjacent the pilot end 16. The working length 18 may have a length of from about 2 mm (0.08 inches) up to the full length of the shank 12, i.e. about 30 mm (1.2 inches). However, in the illustrated embodiment, the working length 18 has a length sufficient to extend substantially the full depth of a tooth root canal as illustrated in FIG. 1, which is about 16 mm (0.63 inches).

The outer peripheral surface of the working length 18 is tapered, so as to define an included angle A of between about ½ and 4 degrees. Also, in the embodiment of FIGS. 1–4, the working length 18 includes two continuous helical flutes 21,22 formed in the peripheral surface, and as best seen in FIGS. 3 and 4, each of the flutes 21,22 defines a curved concave wall when viewed in transverse cross section, and each wall includes a pair of helical shoulders 21d, and 22c, 22d, at the peripheral surface and which face in generally opposite axial directions. The shoulders 21c, 21d, 22c, 22d each intersect the periphery of the shank at an angle of about 90° to a tangent to the shank at the point of intersection, to form what is commonly referred to as a substantially zero or neutral rake angle. Stated in other words, each shoulder lies substantially on a radius of the shank as seen in FIG. 3, so as to form a sharp cutting edge. Each of the flutes also defines a bottom or base 21b, 22b, respectively, at the point of maximum depth from the peripheral surface.

The flutes 21, 22 have the same helix angle, and they are non-uniformly separated in the axial direction. More particularly, the flutes 21, 22 define a relatively broad helical land and a relatively narrow helical surface. Described further, it may be said that the second flute 22 is closely adjacent the first flute 21 on the side of the first flute toward the pilot end 16 so as to define the relatively narrow helical surface 24 therebetween. Also, the second flute 22 is widely spaced from the first flute 21 on the side of the second flute 22 toward the pilot end 16 so as to define the relatively broad helical land 26 therebetween.

In the embodiment of FIGS. 1–4, the two flutes 21, 22 are contiguous and thus the helical surface 24 has no significant axial dimension and it is in the form of a sharp helical edge. Also, as illustrated in FIG. 4, the helical land 26 has an axial length which is about four times the axial cross-sectional width of the flutes. In the embodiment of FIGS. 5–7, the helical surface 24' has a relatively small axial dimension and it thus forms a second helical land. As seen in FIG. 7, the helical land 26 has an axial dimension which is more than about four times greater than the axial dimension of the second helical land 24'. Also, as illustrated in FIG. 7, the second helical land 24' has an axial width which is about one half the axial cross-sectional width of the flutes.

The embodiment of FIGS. 8–10 comprises three helical flutes 21, 22, 23, which are positioned so as to define a relatively broad helical land 26 and a pair of relatively narrow helical surfaces or edges 24". More particularly, the second flute 22 is contiguous to the first flute 21 on the side of the first flute toward the pilot end 16, so as to define a relatively sharp helical edge 24" therebetween. Also, the third flute 23 is contiguous to the second flute 22 on the side of the second flute toward the pilot end 16, so as to define a second relatively sharp helical edge 24" therebetween. Further, the first flute 21 is widely spaced from the third flute 23 on the side of the third flute toward the pilot end and so as to define the relatively broad helical land 26 therebetween.

In a typical example, the length of the working length 18 is about 0.63 inches, with a total of about 18 flute spirals extending along the entire length of the pilot end portion 18, such that the pitch P is 0.63/18 or about 0.035 inches. In the embodiment of FIGS. 1–4, the width F of the flutes is about 0.008 inches and the width L of land 26 is at least about one half the pitch P.

In the drawings and the specification, there has been set forth preferred embodiments of the invention and, although specific terms are employed, the terms are used in a generic and descriptive sense only and not for the purpose of limitation, the scope of the invention being set forth in the following claims.

That which is claimed is:

1. An endodontic instrument adapted for use in performing root canal therapy on a tooth, comprising an elongate shank having a proximate end and an opposite pilot end, and with the elongate shank defining a working length adjacent said pilot end which includes a peripheral surface, and a plurality of continuous helical flutes formed in said peripheral surface so as to extend along the length of said working length, with all of the flutes having the same helix angle, and comprising a first flute, and a second flute closely adjacent the first flute on the side of the first flute toward the pilot end so as to define a relatively narrow helical surface therebetween, and a relatively broad helical land disposed between the second flute and the first flute in a direction from the second flute toward the pilot end.

2. The endodontic instrument as defined in claim 1 wherein said relatively narrow helical surface comprises a relatively sharp helical edge.

3. The endodontic instrument as defined in claim 1 wherein said relatively narrow helical surface comprises a second helical land and wherein the axial dimension of the first mentioned helical land is at least about four times the axial dimension of the second helical land.

4. The endodontic instrument as defined in claim 1 wherein said peripheral surface is tapered toward said pilot end at an included angle of between about ½ and about 4 degrees.

5. The endodontic instrument as defined in claim 1 wherein each of said helical flutes defines a curved concave wall when viewed in transverse cross section.

6. The endodontic instrument as defined in claim 5 wherein each of said flutes defines a pair of helical shoulders at the peripheral surface of said pilot end portion and which face in generally opposite axial directions, and wherein each of said helical shoulders has a substantially neutral rake angle.

7. The endodontic instrument as defined in claim 1 further comprising a handle mounted at said proximate end of said shank.

8. The endodontic instrument as defined in claim 1 wherein said shank is composed of an alloy which comprises at least about 40% titanium and at least about 50% nickel.

9. The endodontic instrument as defined in claim 1 wherein the elongate shank defines a central axis, and wherein the helical surface and the helical land are located at substantially equal radial distances from said central axis at any given location along the working length of the shank.

10. The endodontic instrument as defined in claim 9 wherein the axial width of the helical land is at least about one half the pitch of the flutes.

11. An endodontic instrument adapted for use in performing root canal therapy on a tooth, comprising an elongate shank having a proximate end and an opposite pilot end, and with the elongate shank defining a working length adjacent said pilot end which includes a peripheral surface, and first and second continuous helical flutes formed in said peripheral surface so as to extend along the length of said working length, with the first and second flutes having the same helix angle, and with the second flute being closely adjacent the first flute on the side of the first flute toward the pilot end so as to define a relatively narrow helical surface therebetween, and with the second flute being widely spaced from the first flute on the side of the second flute toward the pilot end and so as to define a relatively broad helical land therebetween.

12. The endodontic instrument as defined in claim 11 wherein said relatively narrow helical surface comprises a relatively sharp helical edge.

13. The endodontic instrument as defined in claim 9 wherein said relatively narrow helical surface comprises a second helical land, and wherein the axial dimension of the first mentioned helical land is at least about four times the axial dimension of the second helical land.

14. The endodontic instrument as defined in claim 9 wherein the elongate shank defines a central axis, and wherein the helical surface and the helical land are located at substantially equal radial distances from said central axis at any given location along the working length of the shank.

15. The endodontic instrument as defined in claim 14 wherein the axial width of the helical land is at least about one half the pitch of the flutes.

16. An endodontic instrument adapted for use in performing root canal therapy on a tooth, comprising an elongate shank having a proximate end and an opposite pilot end, and with the elongate shank defining a working length adjacent said pilot end which includes a peripheral surface, and first, second, and third continuous helical flutes formed in said peripheral surface so as to extend along the length of said working length, with all of the flutes having the same helix angle, with the second flute being closely adjacent the first flute on the side of the first flute toward the pilot end so as to define a relatively narrow first helical surface therebetween, with the third flute being closely adjacent the second flute on the side of the second flute toward the pilot end so as to define a relatively narrow first helical surface therebetween, and a third flute closely adjacent the second flute on the side of the second flute toward the pilot end so as to define a relatively narrow second helical surface therebetween.

17. The endodontic instrument as defined in claim 16 wherein said relatively narrow first and second helical surfaces each comprise a relatively sharp helical edge.

18. The endodontic instrument as defined in claim 16 wherein said relatively narrow first and second helical surfaces comprise first and second helical lands respectively, and wherein the axial dimension of the first mentioned helical land is at least about four times the axial dimension of the first and second helical lands.

19. The endodontic instrument as defined in claim 16 wherein the elongate shank defines a central axis, and wherein the first and second helical surfaces and the helical land are located at substantially equal radial distances from said central axis at any given location along the working length of the shank.

20. The endodontic instrument as defined in claim 19 wherein the axial width of the helical land is at least about one half the pitch of the flutes.

* * * * *

UNITED STATES PATENT AND TRADEMARK OFFICE
CERTIFICATE OF CORRECTION

PATENT NO. : 5,713,736
DATED : February 3, 1998
INVENTOR(S) : Heath et al.

It is certified that error appears in the above-identified patent and that said Letters Patent is hereby corrected as shown below:

Column 3, line 17, after shoulders, insert --21c,--.

Column 5, line 16 and line 21, for the claim reference, numeral "9", each occurrence, should read --11--.

Column 6, line 10, delete beginning with "first helical surface" to and including "surface therebetween." in Column 6, line 14, and insert the following --second helical surface therebetween, and with the first flute being widely spaced from the third flute on the side of the third flute toward the pilot end and so as to define a relatively broad helical land therebetween.--.

Signed and Sealed this

Eighth Day of December, 1998

*Attest:*

BRUCE LEHMAN

*Attesting Officer*    Commissioner of Patents and Trademarks